(12) United States Patent
Giglia et al.

(10) Patent No.: US 8,904,641 B2
(45) Date of Patent: Dec. 9, 2014

(54) METHOD FOR IMPROVED SCALING OF FILTERS

(71) Applicant: EMD Millipore Corporation, Billerica, MA (US)

(72) Inventors: Sal Giglia, Billerica, MA (US); Kevin Rautio, Billerica, MA (US); Mark Blanchard, Billerica, MA (US)

(73) Assignee: EMD Millipore Corporation, Billerica, MA (US)

( * ) Notice: Subject to any disclaimer, the term of this patent is extended or adjusted under 35 U.S.C. 154(b) by 94 days.

(21) Appl. No.: 13/754,928

(22) Filed: Jan. 31, 2013

(65) Prior Publication Data
US 2013/0140224 A1 Jun. 6, 2013

Related U.S. Application Data

(63) Continuation of application No. 12/848,435, filed on Aug. 2, 2010, now Pat. No. 8,387,256.

(60) Provisional application No. 61/274,142, filed on Aug. 13, 2009.

(51) Int. Cl.
*B23P 15/16* (2006.01)
*B01D 69/02* (2006.01)
*B01D 65/10* (2006.01)
*G01N 15/08* (2006.01)

(52) U.S. Cl.
CPC ............... *B01D 69/02* (2013.01); *B01D 65/10* (2013.01); *B01D 2325/20* (2013.01); *G01N 15/0826* (2013.01)
USPC ........... 29/896.62; 29/896.6; 700/29; 700/52; 700/54

(58) Field of Classification Search
CPC ........ B01D 63/02; B01D 63/04; B01D 63/10; B65H 81/00
USPC .................. 29/896.62, 896.6; 700/29, 52, 54
See application file for complete search history.

(56) References Cited

U.S. PATENT DOCUMENTS

| 5,575,910 | A | 11/1996 | Karbachsch |
| 5,618,418 | A | 4/1997 | Demmer et al. |

(Continued)

FOREIGN PATENT DOCUMENTS

| EP | 2123348 A1 | 11/2009 |
| JP | 8-103637 A | 4/1996 |
| JP | 8-103638 A | 4/1996 |
| WO | 00/35567 A1 | 6/2000 |

OTHER PUBLICATIONS

Journal of Membrane Science, vol. 325, 2008, pp. 223-237, "Sterilizing Filtration—Principles and practice for successful scale-up to manufacturing", Rajniak, et al.

(Continued)

*Primary Examiner* — Richard Chang
(74) *Attorney, Agent, or Firm* — Nields, Lemack & Frame, LLC

(57) ABSTRACT

Method of reducing performance variability of membrane scaling devices. Scaling device performance uncertainty is reduced, thereby reducing the scaling safety factor, by specifying a narrow range or subset of the set of all qualified manufactured membranes for installation into scaling devices. In certain embodiments, the scalability factor is reduced by determining where within the performance distribution a particular membrane lies, and adjusting the scaling factor accordingly.

2 Claims, 4 Drawing Sheets

(56) References Cited

U.S. PATENT DOCUMENTS

| | | | |
|---|---|---|---|
| 6,754,543 B1 * | 6/2004 | Wold | 700/52 |
| 7,481,917 B2 * | 1/2009 | Ikeyama et al. | 210/85 |
| 7,972,493 B2 * | 7/2011 | Davis et al. | 205/536 |
| 8,387,256 B2 | 3/2013 | Giglia et al. | |
| 2005/0194317 A1 | 9/2005 | Ikeyama et al. | |
| 2009/0277824 A1 | 11/2009 | Giglia et al. | |
| 2011/0185552 A1 | 8/2011 | Giglia et al. | |

OTHER PUBLICATIONS

BioPharm International, Mar. 1, 2009, pp. 1-13, "Considerations for Scaling-up Depth Filtration of Harvested Cell Culture Fluid", Lutz, et al.

PDA Journal of Pharmaceutical Science and Technology, vol. 61, No. 4, Jul.-Aug. 2007, pp. 314-323, "Scaling from Discs to Pleated Devices", Giglia, et al.

Desalination, vol. 146, 2002, pp. 75-81, "Scale-up of microfiltration systems: fouling phenomena and Vmax analysis", Zydney, et al.

AIChE Annual Meeting, Salt Lake City, 2007, Paper 517a, pp. 1-25, Millipore Corporation, "Scale-up considerations for Buffer and Media Filtration", Kools, et al.

Journal of Membrane Science, vol. 62, 1991, pp. 309-323, "Scale-up of membrane systems from lab data", Gooding.

Membrane Technology, vol. 2000, Issue 117, Jan. 2000, pp. 10-13, "Scale-up and scale-down of membrane-based separation processes", Ball.

Biotechnology and Bioengineering, vol. 55, No. 5, Sep. 1997, pp. 737-746, "Linear Scale Ultrafiltration", Van Reis, et al.

European communication dated Nov. 19, 2010 in corresponding European patent application EP 10171837.7.

Chinese Communication issued Aug. 31, 2012 in corresponding Chinese patent application No. 201010254453.9.

\* cited by examiner

METHOD FOR IMPROVED SCALING OF FILTERS

This application is a continuation of U.S. patent application Ser. No. 12/848,435 filed Aug. 2, 2010, which claims priority of U.S. Provisional Application Ser. No. 61/274,142 filed Aug. 13, 2009, the disclosures of which are incorporated herein by reference.

BACKGROUND

Manufacturers of filtration devices often offer small scale sizing tools for initial evaluation of process streams and for estimating membrane area requirements for the full scale process. Ideally, small scale devices should contain a minimum of membrane area or filtration media to save test fluid while also scaling linearly with their corresponding large scale devices. However, variability in the performance of small scale devices adds uncertainty to the scale-up requirements, resulting in potentially excessive sizing to guard against the possibility that the tested small scale device(s) represented the low end of the performance distribution.

In the case of microfiltration membrane filters, for example, there are many factors that influence membrane performance, including the pore size distribution, the membrane chemistry, membrane thickness, membrane porosity, and others. While membrane manufacturing processes are designed to control all of these factors to maximize uniformity and consistency, there inevitably will be some distribution within normal manufacturing conditions for all of these variables. This membrane variability limits device-to-device performance consistency and therefore limits the precision to which large scale performance can be predicted from small scale performance.

The performance of either large scale samples or small scale filtration devices is often used to estimate the sizing requirements of large scale devices. The use of small scale devices for sizing provides an obvious economic advantage. For example, in sterile filtration of biological fluids, 47 mm or 25 mm membrane discs offer a convenient format for evaluating performance against the discs to large scale membrane devices (e.g., cartridges containing tens to thousands of times more area). For accurate scale-up, the membrane in the small scale device must be representative of the membrane in the large scale devices. However, as in any manufacturing process, there is a finite tolerance in acceptable performance from one lot of membranes to another. The membrane in a scaling device could originate from anywhere within the acceptable performance range. Accordingly, when estimating the required sizing of full scale devices, the variability in membrane performance must be accounted for, necessitating the use of liberal safety factors in scaling estimates.

This can be illustrated by considering a hypothetical distribution of membrane performances as shown in FIG. 1. In this example, average performance (either permeability or throughput capacity) of all membrane lots is normalized to one and the acceptable range of performance is defined as ±30% of the mean. One commonly employed approach is to use a small scale device containing membrane randomly selected from the population, which could perform at anywhere from 0.7 to 1.3. Similarly, a large scale device could perform at anywhere within the same 0.7 to 1.3 range. When scaling from a small scale to a large scale device, the possibility that the small scale device contains high end (1.3) membrane while the large scale device could contain low end (0.7) membrane must be accounted for. That is, a scaling safety factor of 1.3/0.7=1.86 must be applied to ensure that the large scale device requirements are not undersized (see FIG. 2). In this situation, the worst case performance of the full system will be accurately estimated. However, it is also possible that the small scale device could contain membrane at the low end of the distribution (0.7) while the large scale device contains high end (1.3) membrane. Applying the same safety factor would result in a full system performance of (1/3/0.7)/(0.7/1.3), or 3.45. The result would be a filtration system that is oversized by a factor of 3.45. This value is defined as the scaling factor uncertainty ratio ($U_{sf}$) according to the following formula (1):

$$U_{sf}=(F_h/S_l)/(F_l/S_h)=(F_h/F_l)*(S_h/S_l) \quad (1)$$

where $F_h$ is the full scale high end potential performance, $F_l$ is the full scale low end potential performance, $S_h$ is the scaling device high end potential performance, and $S_l$ is the scaling device low end potential performance.

It therefore would be desirable to reduce the range of scaling device performance in order to lower large scale device requirements and save costs.

SUMMARY

The problems of the prior art have been overcome by the present invention, which provides a method of reducing the range of scaling device performance uncertainty. In certain embodiments, scaling device performance uncertainty is reduced, thereby reducing the scaling safety factor, by specifying a narrow range or subset of the set of all qualified manufactured membranes or filtration media for installation into scaling devices. In certain embodiments, the scalability factor is reduced by determining where within the performance distribution a particular membrane lies, and adjusting the scaling factor accordingly. Reducing scaling uncertainty results in significant cost savings, realized, for example, by a reduction in the scale-up sizing requirements.

DETAILED DESCRIPTION

Membrane manufacturing processes inherently result in some variability in membrane properties even though materials and process conditions are kept as constant as possible. As a result, procedures have been instituted to classify or "rate" each batch or roll of membranes after manufacture, based on performance. For example, water permeability and throughput capacity tests are often carried out such as by constructing membrane devices using membranes from a given batch, measuring water permeability, and challenging the devices with a solution containing particles of a selected size and concentration to plug the membrane pores. Throughput capacity (volume filtered) within a specified time period, such as 10 minutes, or some flow reduction amount, such as 70% flow reduction, are measured, and relative capacity values are obtained. The membranes from the given batch are then performance rated based upon the results obtained. The performance of filtration media may also be similarly characterized. Filtration media is material that actively separates solids from a solution and/or binds select materials in solution. Types of filter media include: non-woven fabrics, activated carbon, activated clay, cellulose, ceramic, cotton, diatomaceous earth, glass fiber, ion exchange resins, metals, minerals, paper, nylon, sand, synthetic fiber, Teflon, polyethersulfone, polyester, polypropylene, polytetrafluoroethelyne, polyvinylidene fluoride, polyvinylidene chloride, and polysulfone.

In certain embodiments of carrying out the methods disclosed herein, each batch of membranes or filtration media produced is characterized by performance, and a performance distribution is established. From that distribution, a small subset is selected for installation into scaling devices. By specifying only a narrow range of the distribution for scaling devices, the uncertainty in scaling from small scale to large scale devices (which by definition can contain any qualified membrane or filtration media) is minimized.

Figure 3:
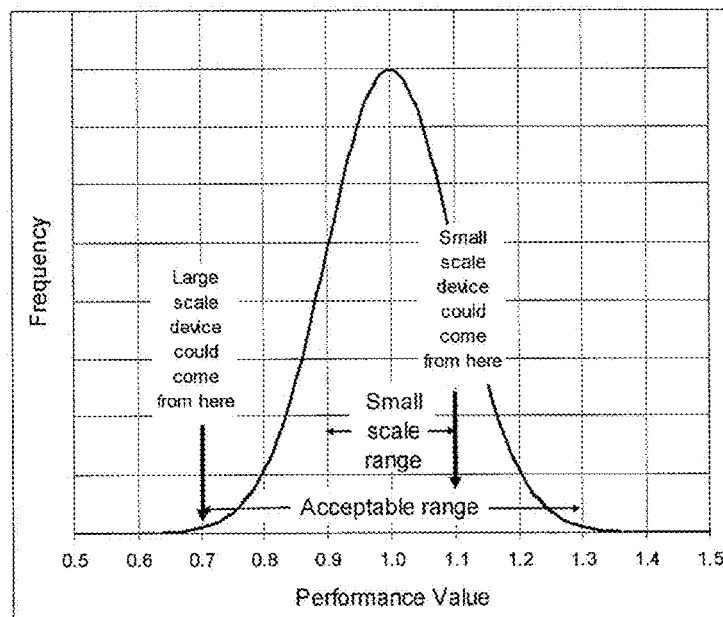
FIG. 3 is a graph of a hypothetical distribution of membrane performance showing possible values for large and small scale devices.

For example, if only the middle third of the distribution is selected for small scale devices, as illustrated in FIG. 3, then the performance of the small scale device will range from 0.9 to 1.1. Since the large scale devices will range from 0.7 to 1.3, the scaling safety factor will be, (in accordance with equation (1), where $S_h$ becomes the scaling device high end potential performance within the subset of the distribution, and $S_l$ becomes the scaling device low end potential performance within the subset of the distribution), (1.3/0.9)/(0.7/1.1)=2.3. In this example, this method results in about a 35% savings in scale-up sizing requirements compared to conventional random membrane selection used for scaling devices.

Figure 4:
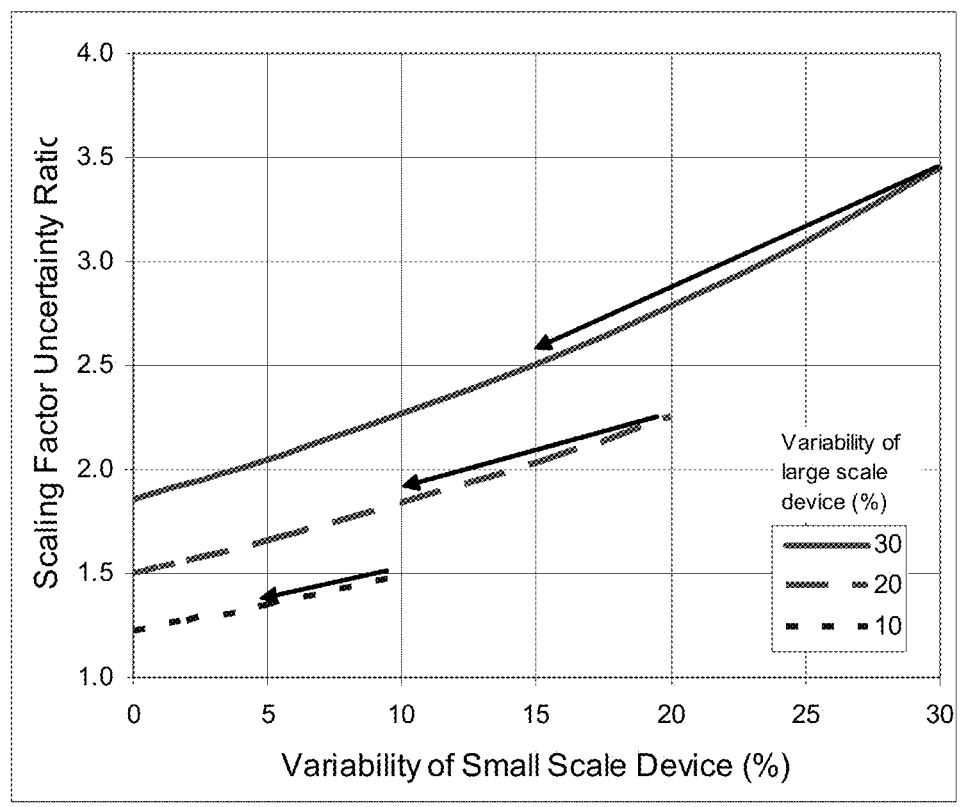
FIG. 4 is a graph of small scale device variability vs. scaling factor uncertainty ratio.

FIG. 4 shows scaling safety factor as a function of small scale performance range for several levels of membrane variability. The current state of the art is defined by the upper end of each curve. The method disclosed herein allows for reduced scaling uncertainty as illustrated by the arrows in FIG. 4.

Figure 1:
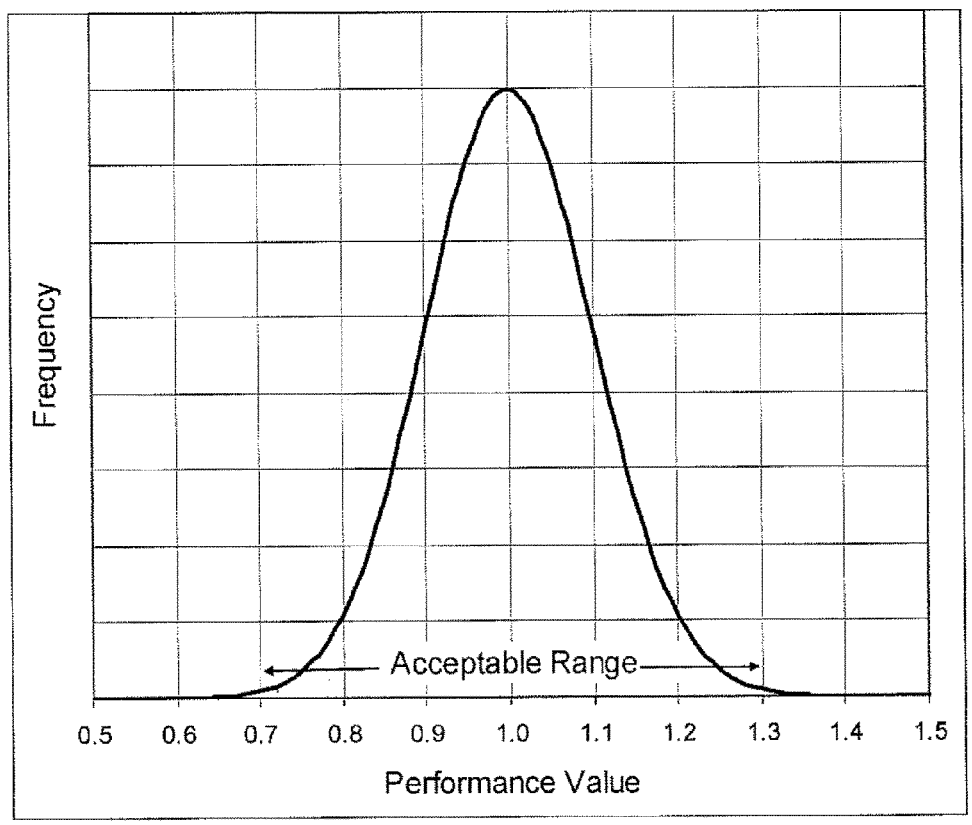
FIG. 1 is a graph of a hypothetical distribution of membrane performance showing an acceptable range.
Figure 2:
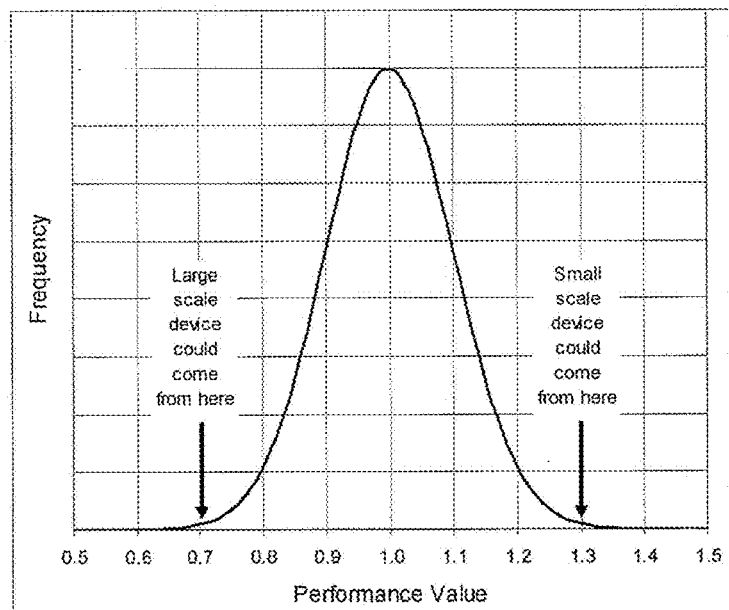
FIG. 2 is a graph of a hypothetical distribution of membrane performance showing possible values for large and small scale devices.

In certain embodiments, the scalability safety factor can be minimized by determining where, within the performance distribution, the small scale device lies (using either a surrogate or actual performance qualification test, for example), and then adjusting the scaling factor to account for the specific portion of the distribution that the scaling device came from. In this approach, any membrane can be used in scaling devices. Information about membrane performance is collected and the information is then provided with the finished device. When the scaling device is evaluated, this membrane performance data is used in determining the scaling factor. For example, using the hypothetical distribution in FIG. 1, assume that a specific membrane has a performance value of 0.9. The scaling factor simply would be (0.9/0.7)=1.3. This factor represents the adjustment for the scaling device with respect to the low end of the full distribution. Since the performance range of the scaling device is well defined and known, $S_h$ and $S_l$ are the same, so equation (1) reduces to:

$$U_{sf}=F_h/F_l \quad (2)$$

The scaling factor uncertainty ratio in this case becomes 1.3/0.7, or 1.86, which represents a 46% reduction compared to uninformed membrane selection.

Example 1

A key performance parameter of sterilizing grade membrane filters is water permeability, which relates to the productivity of the device. Water permeability is measured by supplying water to the membrane, maintaining a pressure difference across the membrane, and measuring the water flow rate. Permeability is calculated according to the formula:

$$Lp=Q/(A*\Delta P)$$

where Lp is water permeability, A is the membrane area, and $\Delta P$ is the pressure difference across the membrane. Water permeability is commonly expressed in units of L/(m²-hr-psi) or LMH/psi.

Figure 5:
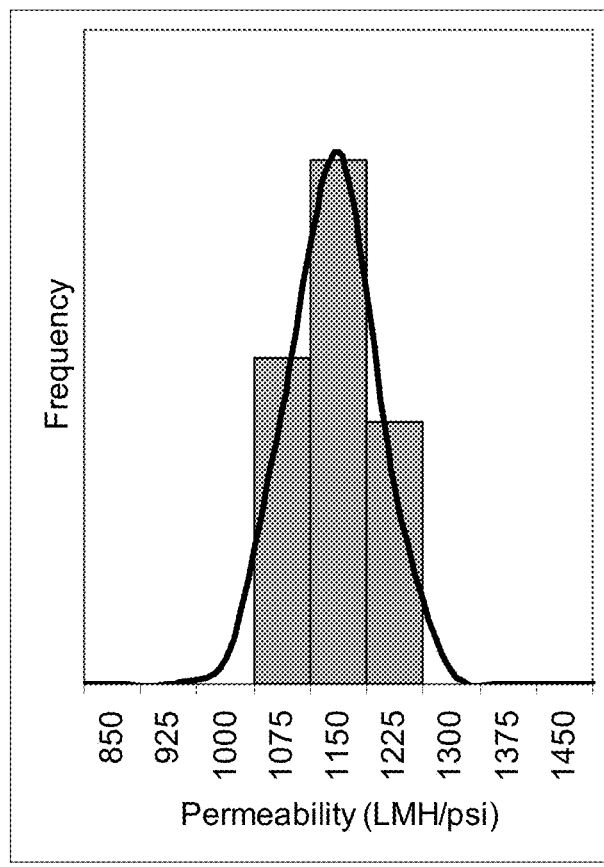
FIG. 5 is a graph of the water permeability distribution of a set of pleated cartridges in accordance with Example 1.

The water permeability was measured on a representative set of pleated cartridges each containing about 0.5 m² of polyethersulfone membrane with a nominal pore size of 0.2 μm. A plot of the distribution is shown in FIG. 5. Water permeability ranged from about 1000 LMH/psi to about 1300 LMH/psi. A subset of the membranes contained in the entire population was selected for installation into small scale disc devices containing 0.0034 m². The selected subset range was restricted to membranes with between about 1100 and 1200 LMH/psi, which constituted about half of the entire membrane population. In accordance with equation 1, the scaling factor uncertainty ratio using any membrane in the population (prior art method) is (1300/1000)*(1300/1000)=1.69. Using the method of this invention, the scaling factor uncertainty ratio was reduced to (1300/1000)*(1200/1100)=1.42, which represents a 16% improvement in scaling factor uncertainty and which translates directly to a proportionally smaller sized full size system compared to the prior art.

Example 2

From the water permeability distribution of Example 1, a single membrane that had been characterized for water permeability was selected from the entire population of membranes. Since the water permeability of this membrane was known, equation 2 was applicable and the scaling factor uncertainty ratio was 1300/1000=1.3, represents a 23% improvement in scaling factor uncertainty compared to the prior art.

What is claimed is:

1. In combination, a plurality of membranes having a first performance distribution, a filtration scaling device and a full scale filtration device related to said filtration scaling device by a scaling factor, said filtration scaling device having a high end potential performance and a low end potential performance within said performance distribution, said full scale filtration device also having a high end potential performance and low end potential performance within said first performance distribution, said filtration scaling device comprising a scaling device membrane selected from said plurality of membranes and having a known range of performance within said performance distribution that is a subset of said first performance distribution; said full scale filtration device comprising a full scale device membrane selected such that said scaling factor is directly proportional to the product of said full scale filtration device high end potential performance within said distribution and the filtration scaling device high end potential performance within said subset of said distribution, and inversely proportional to the product of the filtration scaling device low end potential performance within said subset of said distribution and the full scale filtration device low end potential performance within said distribution.

2. The combination of claim 1, wherein said scaling factor is the product of the full scale filtration device high end potential performance within said distribution and the filtration scaling device high end potential performance within said subset of said distribution, divided by the product of the filtration scaling device low end potential performance within said subset of said distribution and the full scale filtration device low end potential performance within said distribution.

\* \* \* \* \*